US006532071B2

(12) United States Patent
Zare et al.

(10) Patent No.: US 6,532,071 B2
(45) Date of Patent: *Mar. 11, 2003

(54) ANALOG DETECTION FOR CAVITY LIFETIME SPECTROSCOPY

(75) Inventors: Richard N. Zare, Stanford, CA (US); Charles C. Harb, Palo Alto, CA (US); Barbara A. Paldus, Mountain View, CA (US); Thomas G. Spence, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 09/755,253

(22) Filed: Jan. 4, 2001

(65) Prior Publication Data

US 2001/0003482 A1 Jun. 14, 2001

Related U.S. Application Data

(63) Continuation of application No. 09/273,195, filed on Mar. 19, 1999.

(51) Int. Cl.$^7$ .............................................. G01N 21/17
(52) U.S. Cl. ...................... 356/437; 356/440; 250/343
(58) Field of Search .............................. 356/437–440, 356/432; 250/343

(56) References Cited

U.S. PATENT DOCUMENTS 5,903,358 A * 5/1999 Zare et al. .................. 356/437

* cited by examiner

*Primary Examiner*—Frank G. Font
*Assistant Examiner*—Amanda Merlino
(74) *Attorney, Agent, or Firm*—Lumen Intellectual Property Services, Inc.

(57) ABSTRACT

An analog detection system for determining a ring-down rate or decay rate $1/\tau$ of an exponentially decaying ring-down beam issuing from a lifetime or ring-down cavity during a ring-down phase. Alternatively, the analog detection system determines a build-up rate of an exponentially growing beam issuing from the cavity during a ring-up phase. The analog system can be employed in continuous wave cavity ring-down spectroscopy (CW CRDS) and pulsed CRDS (P CRDS) arrangements utilizing any type of ring-down cavity including ring-cavities and linear cavities.

20 Claims, 11 Drawing Sheets

OFFSET SUMMING

AGC

ANALOG DETECTION FOR CAVITY LIFETIME SPECTROSCOPY

CROSS-REFERENCE TO RELATED APPLICATIONS

This application is a continuation of copending application No. 09/273,195 filed Mar. 19, 1999, which is herein incorporated by reference.

STATEMENT REGARDING FEDERALLY SPONSORED RESEARCH OR DEVELOPMENT

This invention was developed with government support provided by the Department of Energy under contract No. DE-FG03-92ER14303 and ARPA-ONR contract No. N00014-92-J-1903. The government has certain rights in this invention.

FIELD OF THE INVENTION

This invention relates to the field of spectroscopy, and in particular to analog electronics for determination of ring-down and ring-up rates in lifetime cavities, also known as ring-down cavities.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light source intensity that are translated into noise in the absorption signal. For general information on traditional spectroscopy methods see for example Dereniak and Crowe, *Optical Radiation Detectors*, John Wiley & Sons, New York, 1984, and Demtroder, *Laser Spectroscopy*, Springer, Berlin, 1996.

Cavity lifetime spectroscopy, otherwise known as Ring-Down Spectroscopy (CRDS), a technique first described by O'Keefe and Deacon in an article in *Rev. Sci. Instrum.* 59(12):2544–2551 (1988), allows one to make absorption measurements with sensitivities on the order of one part per ten million ($1:10^7$) to one part per billion ($1:10^9$) or higher. For general information on CRDS see U.S. Pat. No. 5,528,040 by Lehmann, as well as the articles by Romanini and Lehmann in *J. Chem. Phys.* 102(2):633–642 (1995), Meijer et al. in *Chem. Phys. Lett.* 217(1–2):112–116 (1994), Zalicki et al. in *App. Phys. Lett.* 67(1):144–146 (1995), Jongma et al. in *Rev. Sci. Instrum.* 66(4):2821–2828 (1995), and Zalicki and Zare in *J. Chem. Phys.* 102(7):2708–2717 (1995).

In a CRDS system, the sample (absorbing material) is placed in a high-finesse stable optical resonator or ring-down cavity having an input coupling mirror and an output coupling mirror. Light admitted into the ring-down cavity through the input coupler circulates back and forth multiple times setting up standing waves having periodic spatial variations. Light exiting through the output coupler is proportional to the intracavity light intensity.

After the input light source is terminated, the radiant energy stored in the ring-down cavity decreases in time (rings-down). For an empty cavity, the stored energy follows an exponential decay characterized by a ring-down rate that depends only on the reflectivity of the mirrors, the separation between the mirrors and the speed of light in the cavity. If a sample is placed in the resonator, the ring-down is accelerated; under suitable conditions, the intracavity energy decays almost perfectly exponentially. An absorption spectrum for the sample is obtained by plotting the ring-down rate R or the reciprocal of the ring-down decay constant $1/\tau$ versus the wavelength $\lambda$ of the incident light.

In comparison to conventional spectroscopic techniques, CRDS promises to achieve extremely high detection sensitivity because the ring-down rate $1/\tau$ is not a function of the intensity of the incident light. In other words, intensity fluctuations of the incident light are not related to the ring-down rate in the ring-down cavity and thus do not directly affect the CRDS measurement.

In conventional absorption measurements, when light passes through a sample of length l, the ratio of the transmitted and incident intensities, $I_t$ and $I_o$, satisfies Beer's law:

$$\Delta I/I_o = (I_o - I_t)/I_o = 1 - e^{\alpha l},$$

where $\alpha$ is the absorption coefficient of the sample. Any intensity fluctuations will clearly result in uncertainties in the absorption measured. It is possible to define a minimum detectable absorption (MDAL) based on the intensity noise of the system as follows:

$$MDAL = \sigma_I / l_{\text{eff}},$$

where $\sigma_I$ is the root-mean-square (RMS) intensity noise and $l_{\text{eff}}$ is the effective sample path length (e.g., in a multi-pass absorption measurement cell, the effective sample length can be many times the physical sample path length, since the light beam circulates inside the cell, passing through the sample many times, e.g., up to 500 times or more). Of course, more than one absorption measurement can be taken and the results averaged to reduce the measurement error, however, the fundamental limitation of the system being subject to intensity noise can not be overcome.

In CRDS the measured variable is the decay constant, $\tau$, or the ring-down rate $1/\tau$, and thus the sensitivity is expressed as:

$$S_\tau = \sigma_\tau / (l_{\text{eff}} \sqrt{F}),$$

where F is the number of measurements taken per unit time and the units are expressed in $cm^{-1} Hz^{-\frac{1}{2}}$. Clearly, intensity noise does not figure in this equation. In fact, the ultimate limit of CRDS is the fundamental barrier due to shot-noise inherent in the light beam. Shot-noise results from the discrete nature of photons making up the light beam. The photocurrent produced by a laser beam having power P is $i = RP$ where R is the responsivity of the photodetector. For ideal detection, the photocurrent noise will directly reflect the shot noise of the light. The temporal distribution of shot-noise obeys Poisson statistics and can be expressed as:

$$\sigma_{I, \text{shot-noise}} = \sqrt{(2eI)},$$

where e is the electronic charge ($1.602 \times 10^{-19}$ C).

Theoretically, if CRDS were only limited by shot-noise, the achievable sensitivity would be in the range of $10^{-14}$ $cm^{-1} Hz^{-\frac{1}{2}}$ for a CRDS system having a 50 cm long cavity, a 10 mW continuous-wave (CW) laser with a 10 kHz linewidth and mirrors having losses of 50 ppm.

The actual performance of state-of-the-art CRDS in comparison to other conventional methods is illustrated in Table 1.

TABLE 1

| Spectroscopic Scheme | Typical MDAL ($cm^{-1}$) | Cost | Complexity |
|---|---|---|---|
| Single-pass absorption | $10^{-6}$ | low | simple |
| Multi-pass absorption | $10^{-8}$ | moderate | simple |

TABLE 1-continued

| Spectroscopic Scheme | Typical MDAL (cm$^{-1}$) | Cost | Complexity |
|---|---|---|---|
| ICLAS | $10^{-6}$–$10^{-11}$ | high | difficult |
| FM | $10^{-6}$–$10^{-8}$ | moderate | moderate to difficult |
| P CRDS | $10^{-6}$–$10^{-10}$ | moderate | simple |
| CW CRDS | $10^{-8}$–$10^{-12}$ | low to moderate | simple to moderate |

ICLAS = intracavity absorption spectroscopy; FM = frequency modulation;
P CRDS = pulsed CRDS; CW CRDS = continuous-wave CRDS Most experimental CRDS setups have used pulsed laser sources (P CRDS). However, P CRDS has several practical disadvantages, which preclude shot-noise-limited detection, unless significant effort is made to eliminate them. First, most P CRDS arrangements are limited by the detector noise on the signal, unless special photodetectors such as photomultiplier tubes are used. Unfortunately, photomultiplier tubes can operate only in the ultra-violet to near-infrared wavelength ranges, so that P CRDS in the mid-infrared can be extremely limited. This detection noise is a direct consequence of the limited optical throughput of the high-finesse ring-down cavity. The optical throughput is a function of the ratio of the laser and cavity linewidths. Typical throughputs for pulsed lasers do not exceed 0.01%. In other words, this problem relates to the excess noise present on the ring-down signals, which makes the signal much more difficult to fit accurately. The greater this excess detector noise, the larger the error in the decay rate fit, and hence the greater the error in the absorption loss measurement.

Second, P CRDS is limited by the quality of the mode-matching between the laser beam transverse profile and the ring-down cavity modes. Ideally, only a single transverse and longitudinal cavity mode—the fundamental TEM$_{00}$ mode—is excited in the ring-down cavity. However, because most pulsed laser linewidths tend to be large, multiple longitudinal modes can be excited if the ring-down cavity length is sufficiently large. Moreover, because it is difficult to accurately match the transverse profile of pulsed laser beams to the ring-down cavity mode geometry, multiple transverse modes become excited. Excitation of higher order modes, each having a distinct resonance frequency, can impose a sinusoidal beating which is superposed on the ring-down signal intensity exiting the ring-down cavity, unless all modes are perfectly collected onto a perfectly uniform detector. Physically, such detection is very difficult to implement. In addition, because each cavity transverse mode samples a different portion of the mirrors forming the cavity, each of the modes will experience slightly different reflection and diffraction losses in the cavity. Thus, multiple-mode excitation will also produce a superposition of exponentially decaying signals, each having a slightly different decay constant τ. Hence, trying to determine the decay constant τ for one particular mode, i.e., the fundamental mode, becomes difficult.

Third, the repetition rate of most pulsed laser systems is limited to 100 Hz, so that extensive averaging to improve sensitivity cannot be performed. Moreover, pulsed lasers tend to be bulky and expensive, and therefore impractical for commercial versions of P CRDS.

In addressing the first problem of P CRDS, CW CRDS uses a narrow line-width CW laser with external modulation to limit the optical noise by achieving high overlap between the laser linewidth and the ring-down cavity linewidth. The second problem of mode beating is limited by optically filtering the CW laser beam profile to almost pure TEM$_{00}$. The third problem is addressed by using repetition rates in excess of 1 kHz and up to 10 kHz thus permitting averaging operations. More information about these solutions can be found in D. Romanini et al. "CW Cavity Ring-down Spectroscopy", *Chem. Phys. Lett.*, 264, p. 31 (1997); D. Romanini et al. "Cavity Ring-down Spectroscopy with an External Cavity Diode Laser", *Chem. Phys. Lett.*, 270, p. 538 (1997); B. A. Paldus et al. "Laser Diode Cavity Ring-down Spectroscopy Using an Acousto-optic Modulator", *J. Appl. Phys.*, 82, p. 3199, (1997); and U.S. Pat. No. 5,528,040 to K. K. Lehmann.

Unfortunately, the above improvements introduced in CW CRDS systems to overcome the problems associated with P CRDS have not resulted in significant improvements in the ability to perform spectral scans in real-time and, most importantly, have not managed to significantly improve the sensitivity of the CRDS technique. To date, the highest sensitivities obtained for P CRDS and CW CRDS do not approach the theoretical shot-noise limit. The best arrangements reported so far have sensitivities of about 8×10$^{-10}$ cm$^{-1}$Hz$^{-\frac{1}{2}}$ and 2×10$^{-10}$ cm$^{-1}$Hz$^{-\frac{1}{2}}$ respectively. These figures are still far short of the theoretical limits.

In terms of SNR, a ring-down decay signal is ultimately limited by the fluctuations in photon number that occur for a constant power level. For a power level of 1 mW, the shot-noise-limited SNR is 1.8×10$^6$:1, while for 1 μW the SNR is 5.6×10$^4$:1. These figures are not achieved by state-of-the-art CRDS.

At this point, it should be noted that most CRDS arrangements, with the exception of a boxcar integrator arrangement (see D. Romanini et al., *J. Chem. Phys.*, 102, p. 633 (1995)), as well as most other spectroscopy schemes utilize digital detection electronics. For example, U.S. Pat. No. 5,821,533 to Bingham et al. teaches immediate conversion of an exponentially decaying signal obtained in Ionizing Radiation Spectroscopy to a digital signal. In CRDS the exponentially decaying signal beam or ring-down beam from which the absorption data is derived is first sent to a photodetector which generates a corresponding current or voltage signal. The latter is digitized by a digitizer and passed on to digital processing electronics for determining the decay rate τ from which the absorption is determined. In this arrangement the technical noise of the photodetector and the detection electronics limit detection sensitivity. In fact, in this type of direct detection the ring-down signal decays into the noise of the detection electronics, which causes the electronic noise to become the limiting noise source.

In view of the above problems, it would be desirable to develop a CRDS scheme which permits one to approach the theoretical sensitivity limit of CRDS measurements. Specifically, it would be very desirable to provide a detection system for both P CRDS and CW CRDS whose primary limiting factor in determining the decay rate τ is the shot-noise present in the exponentially decaying ring-down beam.

OBJECTS AND ADVANTAGES OF THE INVENTION

In light of the above, it is a primary object of the present invention to provide a shot-noise limited detection system for determining the decay rate τ of an exponentially decaying ring-down beam or an exponentially building ring-up beam issuing from a lifetime or ring-down cavity. The detection system should be adaptable to CW CRDS as well as P CRDS schemes.

It is another object of the invention to provide a fast detection system for enabling large frequency scan rates.

Furthermore, the system should provide for reliable isolation of the portion of the exponentially decaying signal or exponentially growing signal from which the decay rate or build-up rate is to be computed.

Yet another object of the invention is to ensure that the detection system is compatible with other noise. reducing measures used in CRDS.

The above objects and advantages, as well as numerous additional improvements attained by the detection. system and method of the invention are pointed out below.

SUMMARY OF THE INVENTION

The objects and advantages of the invention are achieved by an analog detection system which determines a ring-down rate or decay rate $1/\tau$ of an exponentially decaying ring-down beam issuing from a ring-down cavity during a ring-down phase. Alternatively, the analog detection system determines a build-up rate of an exponentially growing beam issuing from the cavity during a ring-up phase. The analog system can be employed in P CRDS and CW CRDS arrangements. The analog system has a photodetector for receiving the ring-down beam or ring-up beam and generating from it an exponentially decaying analog signal or an exponentially growing analog signal respectively. The analog signal is fed to a converter which converts it to a linear analog signal. The system is further provided with an analog signal processing circuit for determining the slope of the linear analog signal. The decay rate or ring-up rate is derived by the analog circuit from the slope of the analog signal by using the fact that the slope is generally proportional to the decay rate or the ring-up rate, respectively. For calculation purposes, the analog signal processing circuit can convert the decay rate or ring-up rate to a decay or ring-up rate voltage. An additional element is provided for converting the voltage to a figure indicating the absorption loss of the ring-down cavity.

For detection of the ring-down beam the detection system is equipped with a control element which activates the system during the ring-down phase of the ring-down cavity. In other words, the control element ensures that the detection system performs the above-described operations on the ring-down beam while the cavity is in the ring-down phase. In addition, the analog detection system can have a triggering mechanism for performing its operation during a certain portion of the exponentially decaying analog signal.

For detection of the ring-up beam the detection system is turned on. during the ring-up phase or when the light intensity is building up within the ring-down cavity. The wave form detected during the build-up phase is the reverse of the decay wave-form.

The ring-down cavity is pumped by a pump beam derived from a pump laser. In the P CRDS scheme the laser is a pulsed laser and in the CW CRDS scheme the laser is a continuous-wave laser. In order to determine the absorption spectrum of an absorptive sample placed in the ring-down cavity, the laser is further provided with a frequency adjustment element for altering the frequency of the pump beam. The absorptive sample will alter the decay rate of the ring-down beam or the ring-up rate of the ring-up beam by an amount dependent on the frequency of the pump beam.

In the CW CRDS system a chopping mechanism is provided for interrupting the pump beam during the ring-down phase. In this arrangement the control element activates the detection system during the time when the pump beam is interrupted.

In one embodiment of the invention the pump beam has a certain polarization. For example, the pump beam admitted to the ring-down cavity is of the s-polarization. In this arrangement the p-polarization can be used for performing adjustments, e.g., controlling the length of the ring-down cavity.

An analog detection method for determining the decay rate of an exponentially decaying ring-down beam or the ring-up rate of an exponentially growing ring-up beam in accordance with the invention can be employed in any CRDS in conjunction with other noise reducing measures. Further details on the detection system and method are found below in the description with reference to the attached drawing figures.

DETAILED DESCRIPTION

Figure 1:
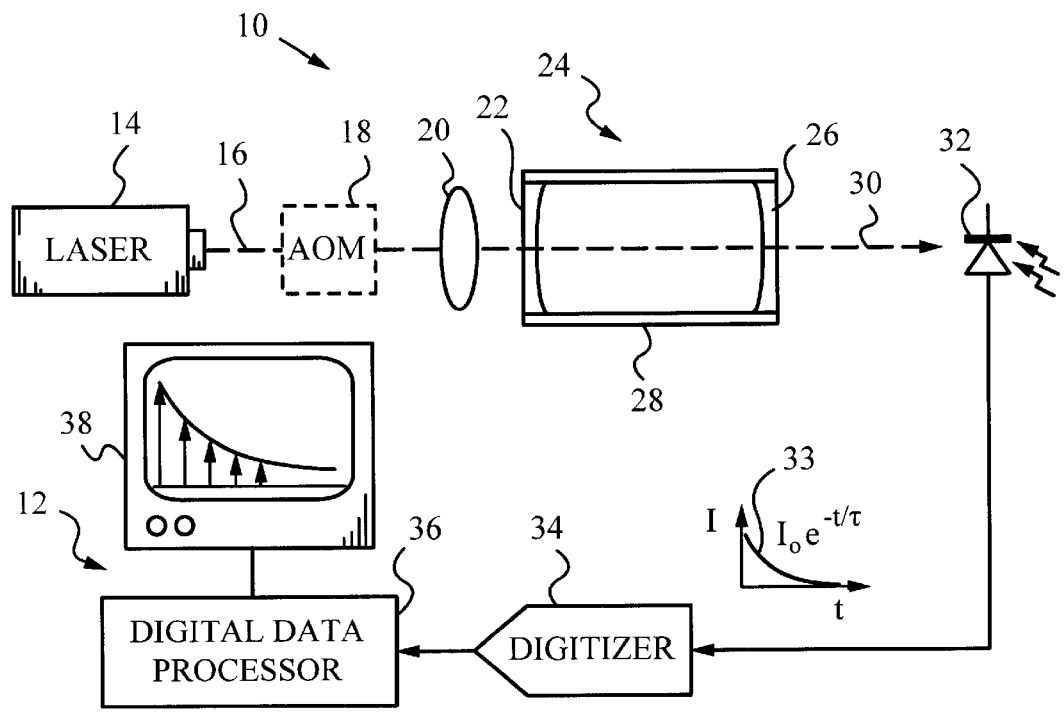
FIG. 1 is a schematic diagram of a representative prior art CRDS arrangement.

To gain a better understanding of the invention, it is instructive to review a typical prior art cavity ring-down spectroscopy (CRDS) arrangement 10 employing a digital detection system 12, as shown in FIG. 1. CRDS 10 is a continuous-wave (CW) system in which a CW laser 14 provides a pump beam 16. An acousto-optic modulator (AOM) 18 passes beam 16 to optics 20, which may include a number of elements but are generally indicated by a focusing lens for reasons of clarity. Optics 20 focus beam 16 on an input coupler 22 of a ring-down cavity 24 to thus inject beam 16 into cavity 24 through input coupler 22. Once inside cavity 24 beam 16 resonates between input coupler 22 and an output coupler 26. Cavity 24 is located in an enclosure 28 which contains a sample, e.g., a gas, whose absorption spectrum is to be analyzed.

When sufficient light buildup is achieved inside cavity 24 pump beam 16 is abruptly shut off by AOM 18. The termination of pump beam 16 commences a ring-down phase of cavity 24. During this time the light inside cavity 24 rings down exponentially at a decay rate $1/\tau$ which depends on the absorption parameters of cavity 24 and the absorption characteristics of the sample gas.

In particular, the absorption parameters of cavity 24 include the length of cavity 24 and reflectivities of couplers 22, 26. The higher the mirror reflectivity and the shorter cavity 24 the lower the absorption losses. The decay rate $1/\tau$ for empty cavity 24 is the baseline decay rate used for reference in determining the absorption of the sample. The baseline is measured over the entire frequency spectrum of interest (i.e., at all frequencies of pump beam 16 which are later used in measuring the sample absorption spectrum) before placing the sample inside cavity 24. The sample introduces its own absorption characteristics and hence increases the decay rate $1/\tau$ of cavity 24 from the baseline. The difference between baseline and the decay rate with the sample present allows one to determine the sample's absorption.

During the ring-down phase an exponential ring-down beam 30 decaying at the decay rate $1/\tau$ issues from cavity 24 through output coupler 26. A photodetector 32 positioned behind output coupler 26 receives ring-down beam 30 and generates an electrical decay signal 33, usually a current, corresponding to ring-down beam 30.

In accordance with the prior art approach, electrical decay signal 33 is first converted to a digital decay signal by a digitizer 34. A digital data processor 36 connected to digitizer 34 processes the digitized decay signal to extract from it the decay rate $1/\tau$ and derive from the latter the absorption of the sample through comparison with the baseline. The result is displayed on a suitable display unit 38. This entire operation is repeated while varying the wavelength of pump beam 16 to obtain and display the complete absorption spectrum of the sample.

Figure 2A:
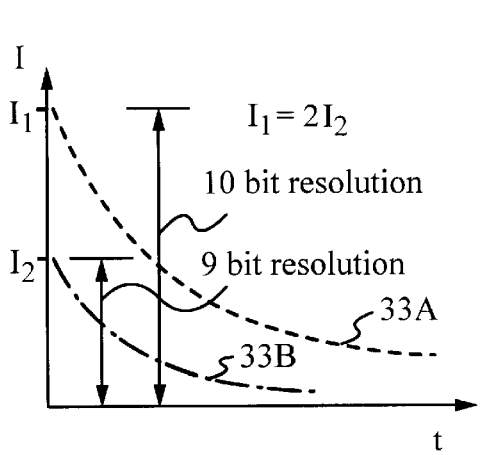
FIG. 2A is a graph illustrating an aspect of the digitization of an exponential decay signal.

When using digitizer 34 for detection, the uncertainty in the decay rate $1/\tau$ depends on the bit resolution achieved in the digitization process. During a spectral scan, the initial intensity $I_0$ of decay signal 33 will differ from the baseline intensity because of the presence of the sample. Specifically, the digitization problem is illustrated in FIG. 2A where decay signal 33A is the baseline with an initial intensity $I_1$ and decay signal 33B is the signal obtained at the sample's absorption peak and has an initial intensity $I_2$. When digitizer 34 is a 10-bit device set to digitize the full range of baseline 33A it loses at least one bit when digitizing decay signal 33B. In other words, decay signal 33B is converted using only 9-bits, thus affecting detection sensitivity and introducing "noise" into the detection system. In this manner, the digital detection system becomes intensity sensitive and eliminates the fundamental advantage of CRDS—that of being a detection technique independent of signal intensity. This problem represents a fundamental limitation of the digitization process.

Additional problems affecting digitizers include their inability to accept the entire decay signal 33 due to limited bandwidth. Hence, a portion of decay signal 33 has to be selected for measurement while the remainder of it is lost. Furthermore, digitizers can not respond quickly to intensity peaks, which means that the regions where signal quality is best for determining decay rate $1/\tau$ may not lend themselves to examination. Finally, even if decay signal 33 were first converted to a linear decay and then digitized, digitizer 34 would inadvertently add noise and non-linearities to the digitized signal. In fact, as the number of bits of digitizer 34 increases so does the non-linearity introduced to the signal.

Figure 2B:
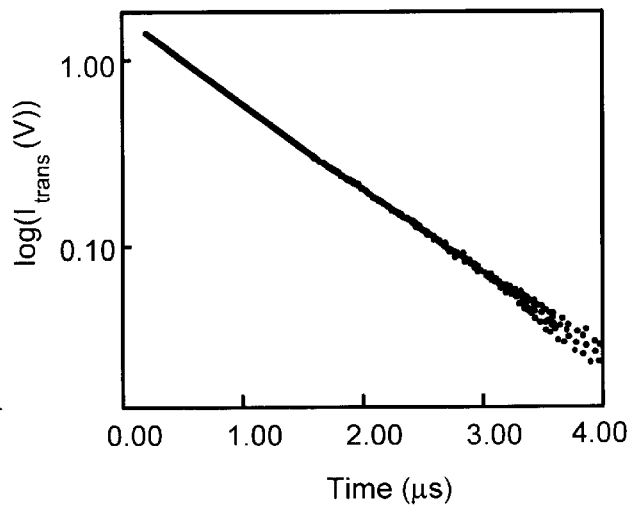
FIG. 2B is a graph illustrating digitization noise observed in a digitized exponential decay signal.

To illustrate these digitization problems in practice, FIG. 2B shows a graph of a digitized exponential decay signal (note that the y-axis is a logarithmic scale). This graph was obtained with a 10-bit digitizing oscilloscope. The noise due to digitization is apparent in the tail portion of the decay.

The problems inherent in the digitization process render digital processing incompatible with CRDS when high sensitivities are desired. In particular, the theoretical shot-noise limit of CRDS can not be realized when using digital signal processing to determine the decay rate $1/\tau$ of decay signal 33. This realization lies at the foundation of the present invention.

Figure 3:
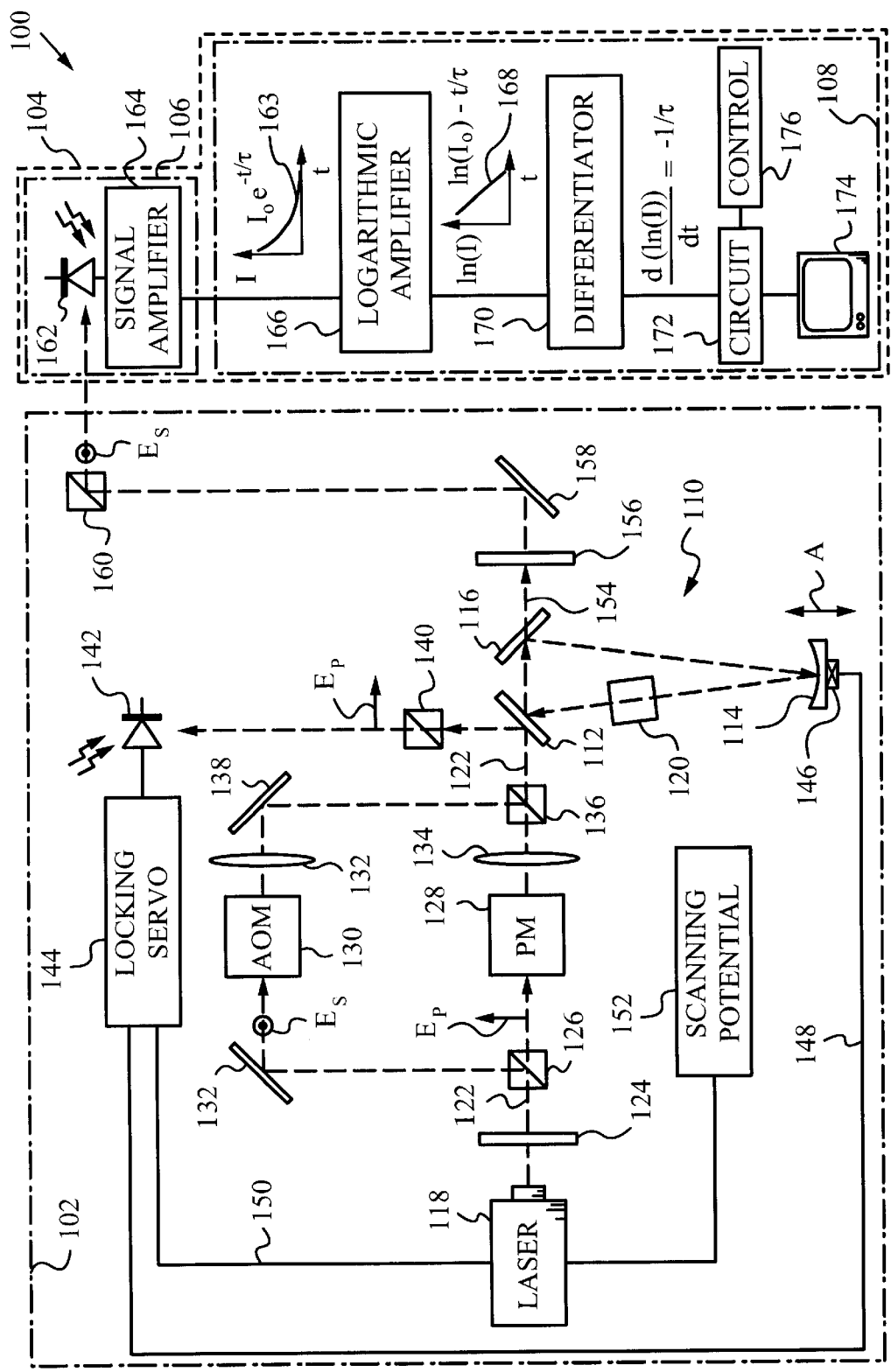
FIG. 3 is a general schematic diagram of a preferred continuous-wave (CW) CRDS arrangement according to the invention.

FIG. 3 illustrates a preferred CW CRDS arrangement 100 according to the invention. For purposes of clarity, CW CRDS arrangement 100 is divided into two parts: an optical measurement system 102 and a detection system 104. Detection system 104 is further subdivided into a photodetection sub-system 106 and a signal processing sub-system 108. It should be noted that arrangement 100 is designed to optimize CW CRDS performance by employing laser-locking, mode matching elements and a cavity having a ring geometry. These additions allow one to minimize the optical noise as well as the noise due to laser beam quality and other common noise sources. Thus, the advantage of shot-noise level sensitivity of detection system 104 is brought to bear. Of course, detection system 104 can also be used in simpler CW CRDS and P CRDS arrangements. For example, detection system 104 can be employed in a swept-cavity CRDS arrangement using only one polarization. It should be kept in mind, however, that in situations where other noise sources are present in the CRDS system, the advantage of shot-noise level detection sensitivity may not be as important. Hence, it is preferable to employ detection system 104 in a CRDS arrangement which eliminates most common noise sources.

Optical measurement system 102 has a high-finesse ring-down cavity 110 set up between three mirrors 112, 114 and 116. Cavity 110 may be located within an enclosure if designed for measuring the absorption of gases or it may not have an enclosure if designed for measuring non-volatile samples, e.g., thin films. Mirror 112 is a plano-plano mirror serving as an input coupler and mirror 116 is a plano-plano mirror serving as an output coupler. Mirror 114 is a concave mirror. Ring-down cavity 110 has a ring cavity geometry, which is the most preferred type of cavity for practicing CRDS. Of course, CRDS in accordance with the invention can also be practiced in a linear cavity. A person of average skill in the art will be able to adapt optical measurement system 102 to a linear cavity.

Optical measurement system 102 is equipped with a pump laser 118 which is preferably a high-quality, narrow linewidth laser tunable over a wavelength range of interest. In particular, pump laser 118 generates a pump beam 122 whose wavelength range is selected to include the absorption peak(s) of interest of an absorptive sample 120 placed in ring-down cavity 110. For example, laser 118 is a Nd:YAG laser having an output power of 300 mW and a tunable range from 1064.44 nm to 1064.58 nm. This wavelength range permits one to study an absorption spectrum of a $CO_2$ transition at 1064 nm. Of course, this is an exemplary range used for demonstration purposes only.

A half-wave plate 124 followed by a polarizing beam splitter (PBS) 126 are placed in the path of beam 122. Beam 122 contains an s-polarization $E_S$ and a p-polarization $E_P$ with respect to ring-down cavity 110. Polarizations $E_S$ and $E_P$ are orthogonal to each other and their relative intensities can be adjusted with the aid of half-wave plate 124.

PBS 126 separates polarization $E_S$ from polarization $E_P$. Polarization $E_P$ is passed to a phase modulator (PM) 128 while polarization $E_S$, after reflection from a mirror 132, is passed to an acousto-optic modulator (AOM) 130. In preferred arrangement 100 AOM 130 has two functions. First, it frequency shifts polarization $E_S$ as necessary to allow both polarizations $E_P$ and $E_S$ to be simultaneously resonant in ring-down cavity 110. Second, AOM 130 is also used to switch polarization $E_S$ on and off, i.e., AOM 130 is used to terminate polarization $E_S$ at required times.

PM 128 is used to generate feedback from ring-down cavity 110 to allow one to lock laser 118 to cavity 110. This can be performed in accordance to the Drever technique described by R. Drever et al. in. *Applied Physics B*, 1983, B31, pg. 1997. This technique relies on deconvolving or separating the response of a cavity from the sidebands in the reflected signal to generate an error signal. The error signal is used by a servo to change either the laser line frequency or the cavity line frequency (e.g., by changing the length of the cavity with the aid of an appropriate actuator arranged to move at least one of the cavity's mirrors).

Both polarizations $E_S$ and $E_P$ pass through mode-matching optics 132, 134 generally indicated by lenses, and are recombined as beam 122 by a PBS 136 after polarization $E_S$ is reflected by a mirror 138. Mode-matching optics 132, 134 ensure modal purity of recombined beam 122. Ideally, recombined beam 122 is in the $TEM_{00}$ mode thus eliminating mode-beating and the associated problems discussed above.

Beam 122 is injected into ring-down cavity 110 through input coupler 112. $E_S$ polarization is used for absorption measurement and $E_P$ polarization is used for locking laser 118 to cavity 110. Since cavity 110 is a ring cavity $E_P$ and $E_S$ polarizations reflected by cavity 110 do not retrace the path of original beam 122. Hence, well-known feedback problems associated with portions of pump beam 122 being reflected back to laser 118 are avoided. Instead, $E_P$ and $E_S$ polarizations reflected from cavity 110 pass through input coupler 112 at an angle to beam 122 and $E_P$ polarization is isolated from $E_S$ polarization by a PBS 140.

Reflected $E_P$ polarization is detected by a photodetector or photodiode 142 and converted into an adjustment signal. The adjustment signal from photodiode 142 may be amplified by an amplifier (not shown) as necessary and delivered to a locking servo 144. Locking servo 144 uses the adjustment signal to lock laser 118 to cavity 110.

In fact, servo 144 sends a high frequency portion of the adjustment signal via connection 148 to a first actuator 146, e.g. a piezoelectric actuator (PZT). PZT 146 moves mirror 114 as indicated by arrow A and thereby adjusts the length of cavity 110. This adjustment is performed for high frequency disturbances, e.g., in the kHz range. In the present embodiment the unity gain frequency, i.e., the center frequency for high frequency adjustments was set at 60 kHz. Low frequency adjustment signals are divided into very low and low frequency; the first having unity gain at 1 Hz and the second having unity gain at 100 Hz. The very low frequency adjustment signals are delivered via connection 150 to the temperature control (not shown) of laser 118. The temperature control adjusts the temperature of laser 118 and thus adjusts. the wavelength of beam 122. The low frequency adjustment signals are sent to PZT 146 via connection 148 to adjust the length of cavity 110.

A person of average skill in the art will recognize that this method of locking laser 118 to cavity 110 can be modified in many ways. Also, other locking techniques known in the art may be utilized. However, it is important that laser 118 be locked to cavity 110 with sufficient accuracy to ensure a high and stable optical throughput of light through cavity 110. In other words, the locking should overcome the problem of intensity fluctuations produced during coupling between laser 118 and cavity 110, thus eliminating coupling-related noise described in the background section. Furthermore, the locking should be stable for a sufficiently long period of time, i.e., for a period of at least one scan of sample 120.

A scanning unit 152 is connected to laser 118 for the purpose of tuning the wavelength of beam 122 over the tunable range. Of course, varying the length of cavity 110 with the aid of PZT 146 can also be employed for altering the resonant wavelength within cavity 110 and thus achieving some wavelength tuning or scanning. Typically, however, high speed scans (e.g., in the ranges of hundreds of MHz/s) are most effectively performed with the aid of unit 152. A person of average skill in the art will recognize and implement the most viable scanning method in a given situation.

Once sufficient light buildup in cavity 110 is achieved, AOM 130 is switched to interrupt the passage of $E_S$ polarization. When this is done, $E_S$ polarization built-up inside cavity 110 rings down. The time during which this ring down occurs is the ring-down phase. In particular, a ring-down beam 154 exhibiting an exponentially decaying form and containing both the $E_S$ and $E_P$ polarizations issues from cavity 110 during the ring-down phase. A half-wave plate 156 positioned in the path of ring-down beam 154 adjusts the relative intensities of polarizations $E_S$ and $E_P$ of ring-down beam 154.

A mirror 158 reflects ring-down beam 154 to a PBS 160 which eliminates $E_P$ polarization and sends $E_S$ polarization to photodetection sub-system 106. It should be remembered that only $E_S$ polarization is used for ring-down measurements while $E_P$ polarization is used for locking laser 118 to cavity 110.

Of course, a person of average skill in the art will recognize that in alternative embodiments, e.g., ones which do not use $E_P$ polarization for laser-to-cavity locking, the ring-down measurement may be performed on $E_P$ polarization rather than $E_S$ polarization. In some embodiments both polarizations can be used for performing the ring-down measurement, e.g., when cavity 110 is replaced with a linear cavity and the resonant frequency for both polarizations is the same. A person skilled in the art will also recognize that other polarizations besides the linear $E_P$ and $E_S$ polarizations can make up ring-down beam 154. The necessary adjustments which have to be made to accommodate various polarizations of light in ring-down beam 154 are well known in the art.

Referring back to the embodiment of FIG. 3, photodetection sub-system 106 has a photodetector 162 for receiving ring-down beam 154, and specifically $E_S$ polarization, decaying exponentially at a decay rate $1/\tau$ and generating from it a corresponding exponentially decaying analog signal 163. In particular, photodetector 162 converts the photons in ring-down beam 154 to an electrical current 163. By virtue of mode matching and laser locking employed in this preferred embodiment, the main source of noise present in $E_S$ polarization is the shot-noise due to the quantum nature of light. Hence, the main source of noise in electrical current 163 produced by photodetector 162 is the shot noise from beam 154. All other noise is below the technical noise of photodetector 162.

Photodetector 162 is followed by a low-noise amplifier 164 which amplifies the electrical current to a detectable level. Typically, low-noise amplifier 164 will introduce some single-shot noise of its own to the current. However, increasing the power level of beam 122 such that the power level at photodetector 162 is above 800 $\mu W$ ensures that noise in analog signal 163 exceeds any single-shot noise introduced by amplifier 164. In fact, a person of average skill in the art will be able to determine what power level adjustments need to be made in any given situation to maintain the noise produced by photodetection sub-system 106 below the level of shot noise present in analog signal 163.

Photodetection sub-system 106 sends analog signal 163 to signal processing sub-system 108. The latter has a logarithmic amplifier 166 for receiving exponentially decaying analog signal 163 and converting it to a linearly decaying analog signal 168. The linear decay of analog signal 168 is characterized by a constant slope which is equal to or proportional to $-1/\tau$.

A differentiator 170 receives analog signal 168 and differentiates it to obtain its slope. The output of differentiator 170 is thus a constant value of $-1/\tau$. In practice, this value may fluctuate due to any remnant noise in the system, e.g., residual mode-beating effects. A person of average skill in the art will realize that adjustment to optical measurement system 102, and specifically, fine-tuning of mode-matching optics 132, 134 to ensure that beam 122 coupled into cavity 110 is in the $TEM_{00}$ mode will alleviate most of this noise.

A decay rate determination circuit 172, receives the value of the slope of signal 168 and multiplies it by a factor of $-1$ or a negative constant, as required, to obtain the decay rate $1/\tau$. Since the value of the slope undergoes only minor fluctuations, and preferably no fluctuations, digitization and further digital processing is preferred. Hence, circuit 172 includes a digitizer for digitizing the value of the slope and a digital signal processing unit (not shown) for performing the multiplication and for comparing the value of the slope with the baseline slope value to derive the absorption of sample 120. Additionally, the digital processing unit preferably includes statistical analysis functions for evaluating the slope values obtained during one ring-down phase and for evaluating slope values obtained during successive ring-down phases. A person of average skill in the art will be familiar with the functions which need to be implemented in the digital signal processing unit and will also realize that any additional statistical computation capabilities may be included for a thorough analysis of decay signal 163. Alternatively, well-known analog electronics capable of performing the functions of the digital signal processing unit may be utilized.

A display unit 174 is connected to circuit 172 for displaying the results. In particular, display unit 174 preferably displays decay rate $1/\tau$ or the decay constant $\tau$, the absorption of sample 120, and the results of any statistical analysis performed by the signal processing unit.

Preferably, signal processing sub-system 108 is only activated to compute the decay rate $1/\tau$ during the ring-down phase of cavity 110. During the pumping phase or ring-up phase sub-system 108 can be turned off entirely, or the data computed may be disregarded. This shut off function is performed by a gating unit or control element 176 in accordance with well-established electronic techniques. Alternatively, sub-system 108 can be activated during the light build-up phase to measure decay rate $1/\tau$ at that time. This option is discussed in detail below as implemented in the system shown in FIG. 4.

It will be recognized by a person of average skill in the art that CW CRDS arrangement 100 admits of numerous specific designs of analog detection system 104. A few embodiments of detection system 104 with corresponding circuits and signal plots are discussed below for illustrative purposes.

Figure 4:
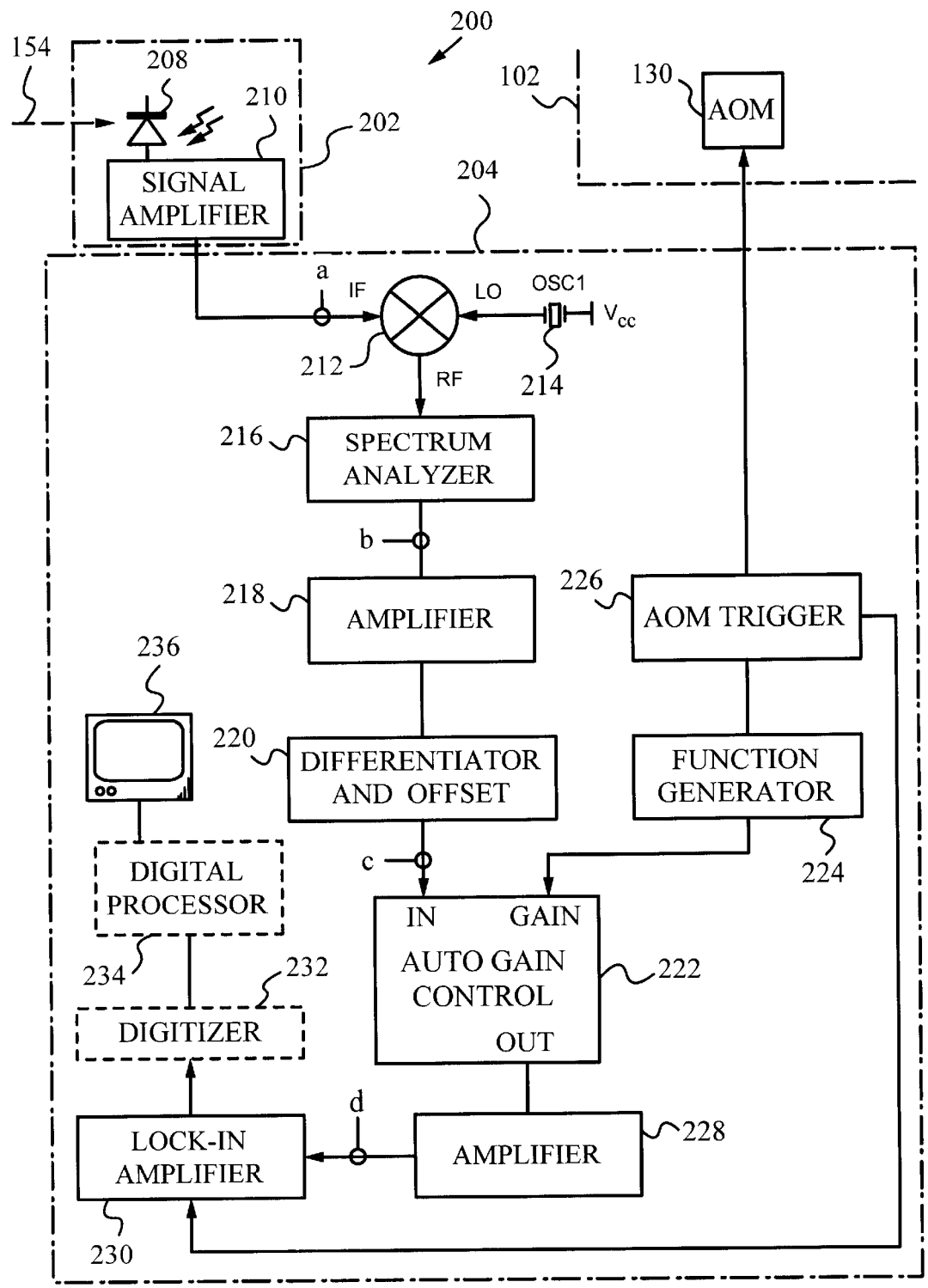
FIG. 4 is a detailed diagram of the detection system of the of the CW CRDS arrangement of FIG. 3.
Figure 5:
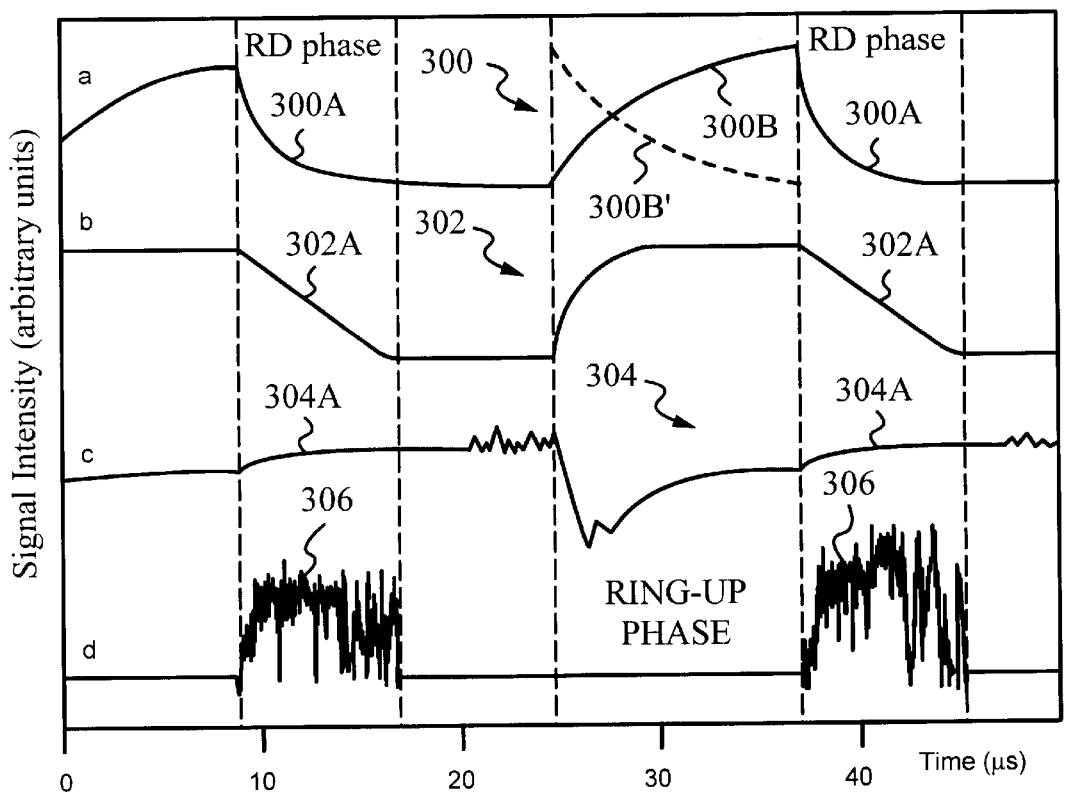
FIG. 5 is a graph of the signals tapped at specific points in the detection system of FIG. 4.

FIG. 4 shows a block diagram of an analog detection system 200 having a photodetection sub-system 202 and a signal processing sub-system 204. Detection system 200 is used with optical measurement system 102. The signals encountered at selected points in system 200 are designated by letters a, b, c, d and are illustrated in the graph of FIG. 5. For clarity and completeness the signals are traced during the ring-down phase as well as during the light buildup phase.

Figure 6:
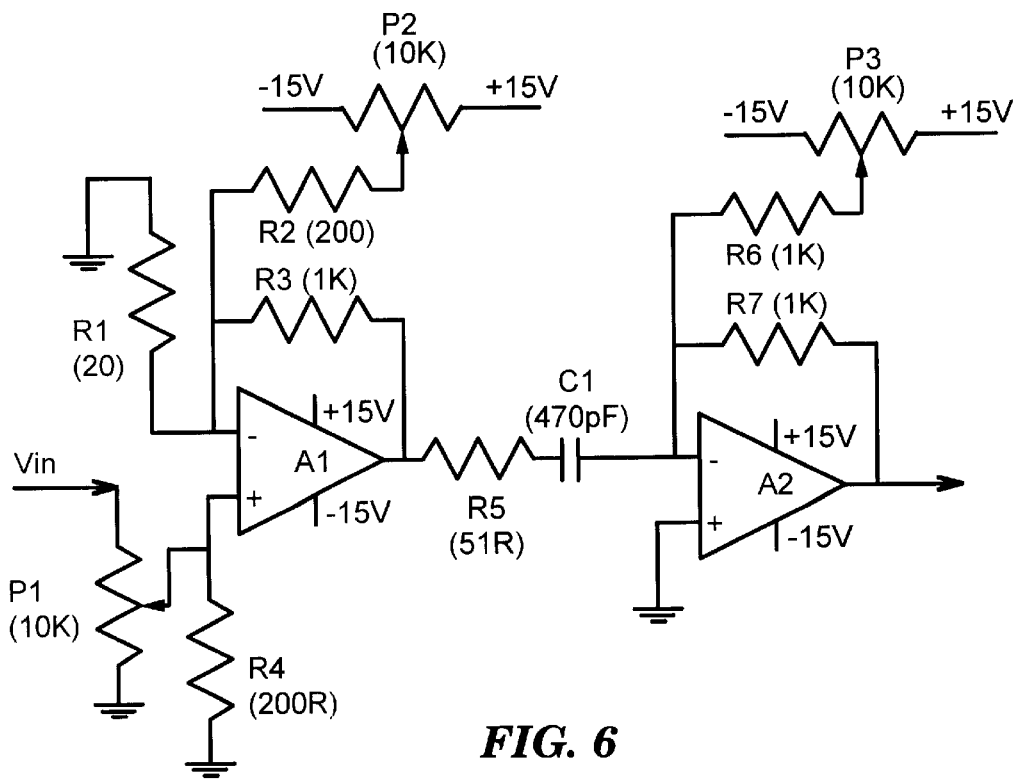
FIG. 6 is a circuit diagram of an exemplary transimpedance amplifier used in the detection system of FIG. 4.

Photodetection sub-system 202 receives ring-down beam 154 issuing from ring-down cavity 110. A photodetector 208 such as a photodiode, a phototransitor or a photomultiplier tube is used for receiving beam 154 and converting it to an electrical signal 300. A signal amplifier 210 amplifies signal 300. At point a signal 300 has the form shown in FIG. 5. The exponentially decaying portion of current signal 300 or an exponentially decaying analog signal 300A is registered during ring-down phases as indicated. The remaining portions of signal 300 correspond to the times when the tail portion of signal 300A drops below measurable threshold and the times when the light is building up in the ring-down cavity. An example of a suitable signal amplifier 210 is a transimpedance amplifier as shown in FIG. 6.

Referring back to FIG. 4, signal 300 is sent from photodetection sub-system 202 to signal processing sub-system 204. Sub-system 204 has a mixer 212 and. a local oscillator 214 such as a voltage-controlled oscillator (VCO) for generating a LO frequency signal in the form of a sine wave. Signal 300 is delivered to mixer 212 as the intermediate frequency (IF) signal and upconverted to a radio-frequency (RF) signal through mixing with the LO frequency signal. The RF signal is then sent to a spectrum analyzer 216 which samples the power level of the RF signal using the LO frequency as the sampling frequency and outputting the resulting power on a logarithmic. scale. Thus, analyzer 216 acts as a logarithmic amplifier of signal 300 and generates a signal 302 which at point b has the form shown in FIG. 5. Clearly, portion 302A of signal 302 represents a linearly decaying analog signal corresponding to the exponential decay signal 300A.

Of course, signal 300 can also be sampled directly at a specified sampling frequency to obtain signal 302 without prior upconversion to an RF frequency. This is possible when using a logarithmic amplifier which does not require an input modulated by a sine wave (LO frequency signal). However, as is known in the art, typical high-speed logarithmic amplifiers can only reliably output the logarithm of an input signal when the latter is modulated by a sine wave. Furthermore, modulating signal 300 with LO frequency and upconverting it to an RF frequency is helpful when using filters (not shown) to eliminate the inherent low frequency noise of photodetector 208. As is known in the art, it is easier to upconvert a signal laden with low frequency noise to a higher frequency and then filter out the noise.

Figure 7:
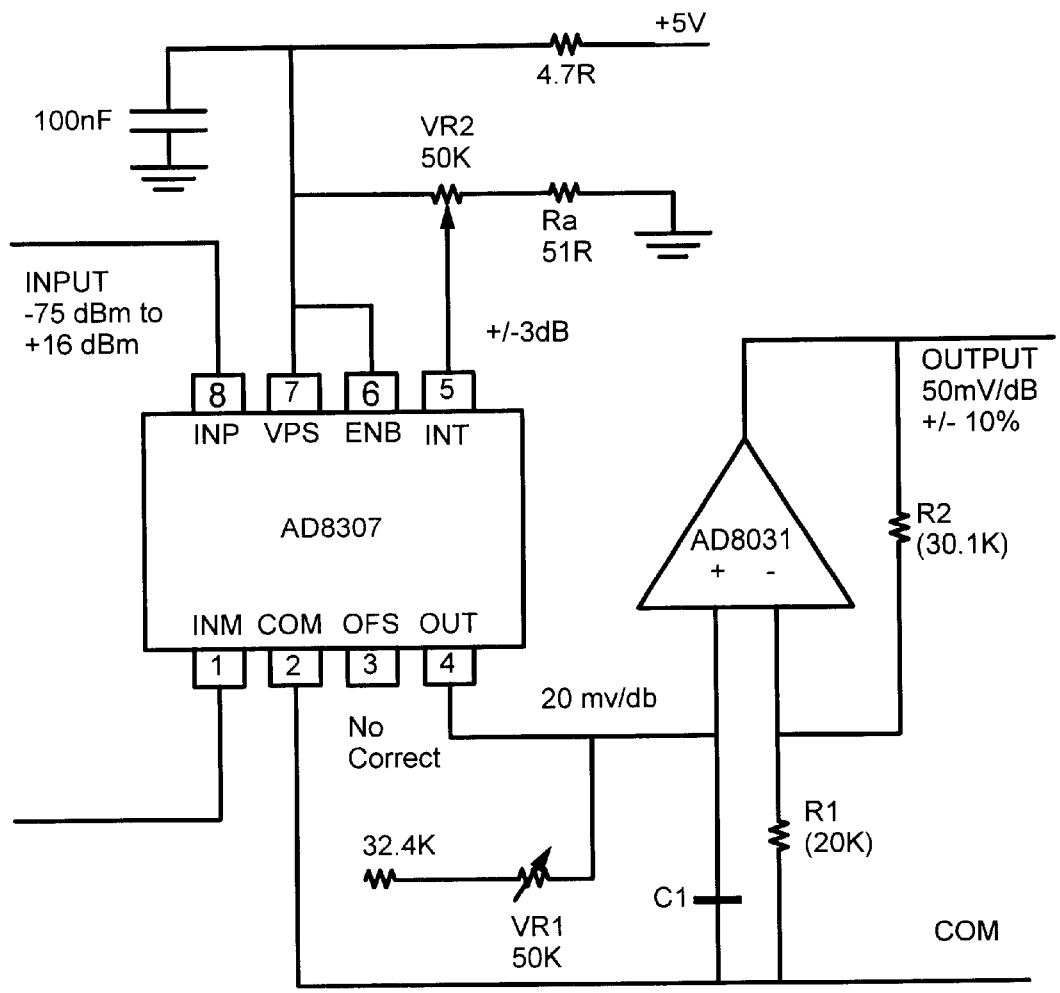
FIG. 7 is a circuit diagram of a logarithmic amplifier suitable for use in a CW CRDS arrangement according to the invention.

In another alternative embodiment, spectrum analyzer 216 can be replaced by a notch filter centered at the LO frequency of VCO 214 and a dedicated logarithmic amplifier. FIG. 7 shows a circuit diagram of a suitable dedicated logarithmic amplifier which can be used for this purpose. The circuit of FIG. 7 is simple and its employment is preferable if detection system 204 is to be low-cost.

Figure 8:
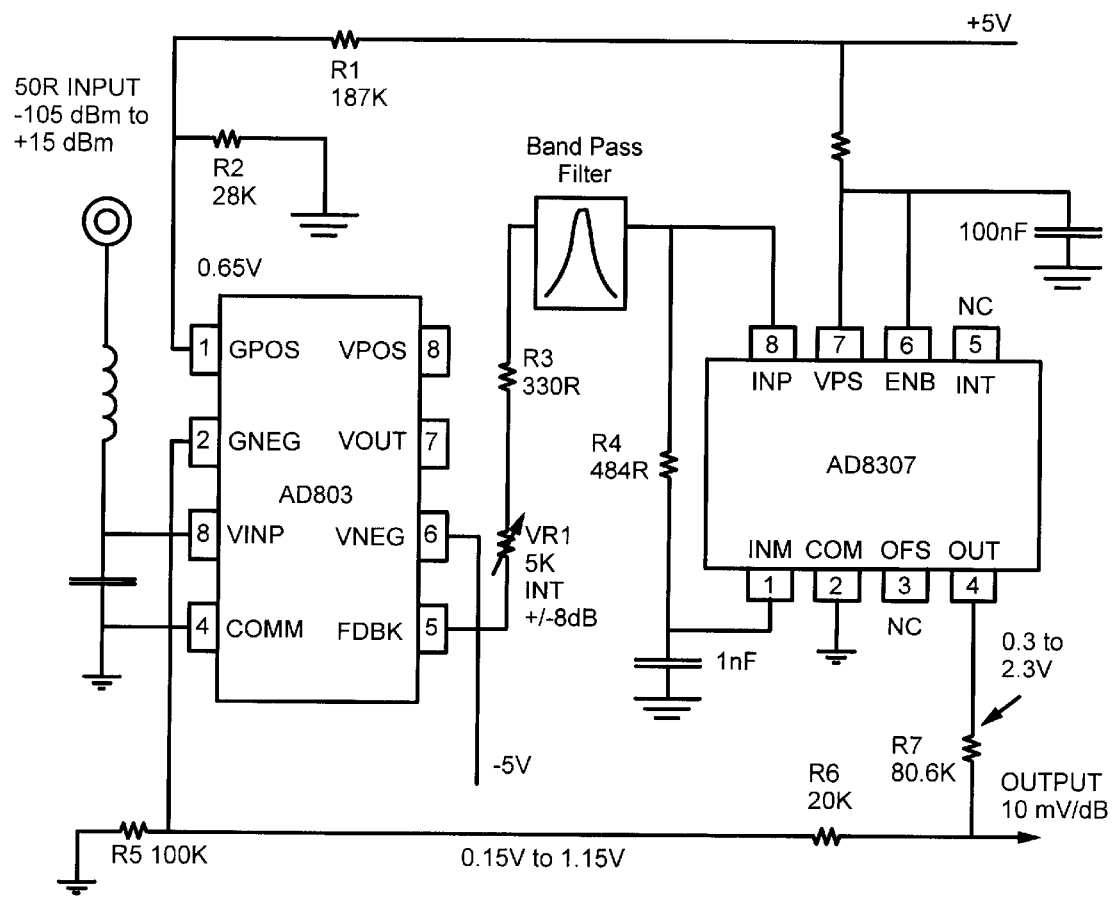
FIG. 8 is a circuit diagram of an equivalent of a spectrum analyzer for use in a CW CRDS arrangement according to the invention.

When a larger dynamic range is required than that achievable by the logarithmic amplifier of FIG. 7, an alternative spectrum analyzer can be used. FIG. 8 shows the circuit diagram of this type of an alternative spectrum analyzer based on both a logarithmic and a precision gain amplifier. A person of average skill in the art will be able to select the best alternative for obtaining signal 302 from signal 300 given the specific design parameters.

Figure 9:
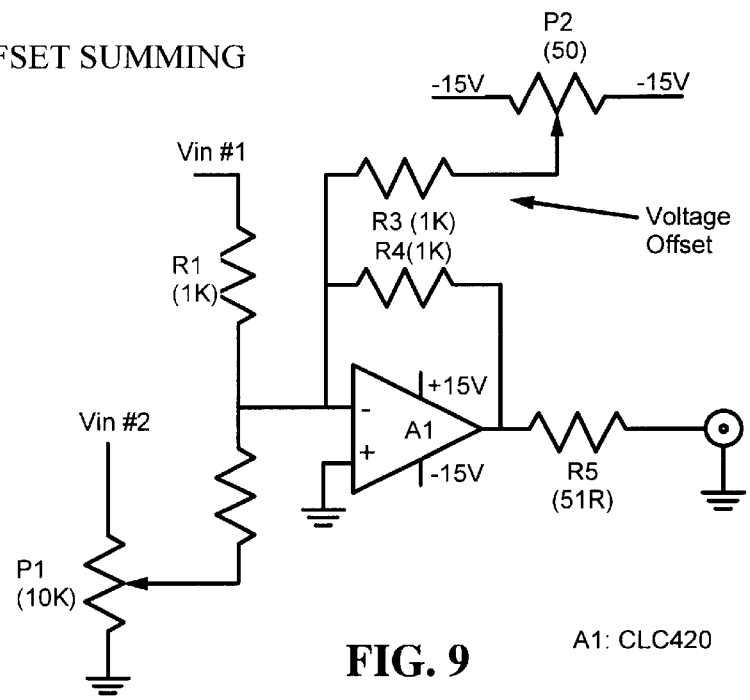
FIG. 9 is a circuit diagram of an offset summing circuit used in the detection system of FIG. 4.

Referring back to the diagram of FIG. 4, amplifier 218 amplifies signal 302 and delivers it to a differentiator and offset unit 220. Unit 220 differentiates signal 302 over the ring-down phase to yield a measured voltage proportional to the decay rate $1/\tau$. In order to better measure small changes in the decay rate $1/\tau$, the measured voltage obtained is summed with an offset voltage to yield a resulting voltage 304 which is close to zero for the duration of the ring-down phase. Using an offset voltage summing procedure for improved accuracy of measurement is well-known in the art. An example circuit for performing the offset summing function is illustrated in FIG. 9. Resulting voltage 304 as registered at point c is shown in FIG. 5. The portion measured during the ring-down phase is indicated by reference 304A.

Figure 10:
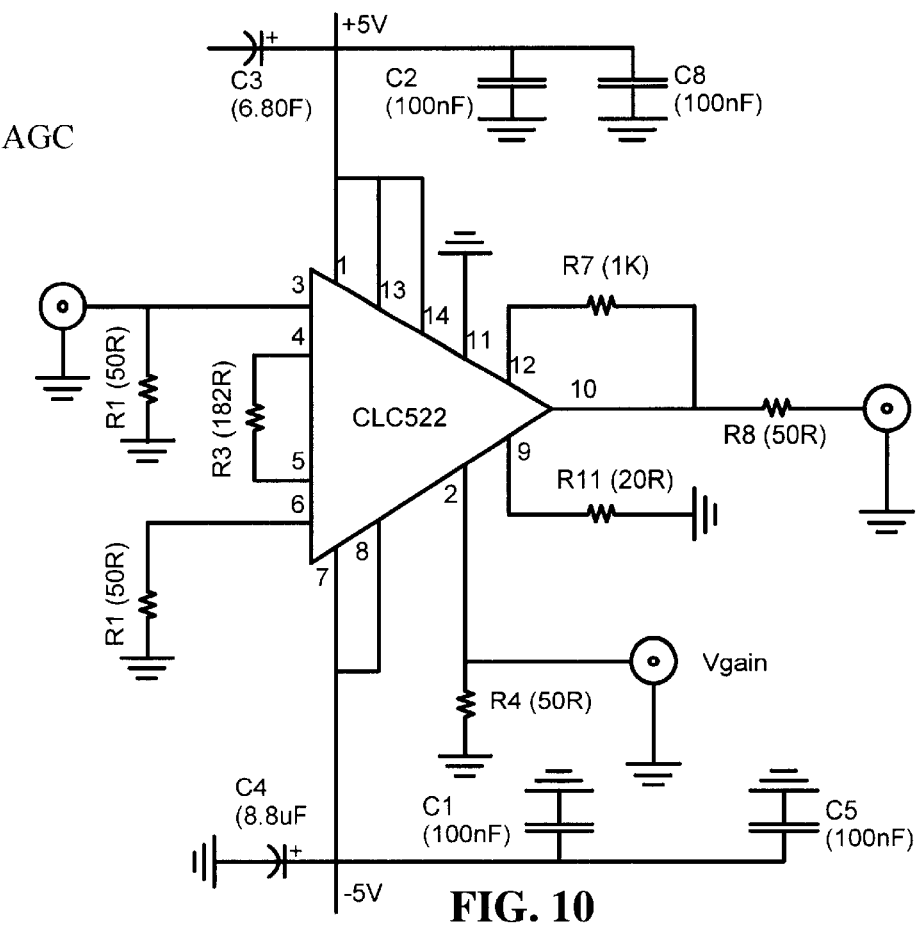
FIG. 10 is a circuit diagram of an automatic gain control (AGC) amplifier used in the detection system of FIG. 4.

The output of unit 220 delivering resulting voltage 304 is connected to an input of a control element 222. In this embodiment element 222 is an automatic gain control (AGC) amplifier. An exemplary circuit diagram of a suitable design of AGC 222 is shown in FIG. 10.

A function generator 224 is connected to a gain input of AGC 222. Function generator 224 itself is connected to an AOM trigger 226.

The function of trigger 226 is to generate a switching signal which is relayed to optical measurement system 102. In particular, the switching signal of trigger 226 is sent to AOM 130 to switch the $E_S$ measurement polarization off to initiate the ring-down phase and to switch the $E_S$ polarization back on to initiate light buildup inside cavity 110. Function generator 224 uses the switching signal from trigger 226 to control the gain of AGC 222. Specifically, when AOM 130 is switched off during the ring-down phase function generator 224 sets the gain of AGC 222 to pass resulting voltage 304. When AOM 130 is switched on and light is building up inside cavity 110 function generator 224 sets the gain of AGC 222 to zero. Consequently, only portion 304A of resulting voltage 304 is passed by AGC 222 to its output. This process is referred to as gating in which AGC 222 acts as a gate allowing resulting voltage 304 to pass only during a gate width corresponding to the duration of the ring-down phase. Of course, the gate can be adjusted to pass only a particular portion of resulting voltage 304, e.g., that corresponding to the initial portion of the ring-down phase, or any portion during which measurement of decay rate $1/\tau$ is determined to yield the best results.

The output of AGC 222 is connected to an amplifier 228 which amplifies resulting voltage 304A to yield a DC signal 306 indicated at point d and shown in FIG. 5. Because of the gating function of AGC 222, DC signal 306 is only produced during the gate width which corresponds to the ring-down phase. DC signal 306 is very sensitive to small changes in the decay rate $1/\tau$, as evidenced by its large fluctuations. This sensitivity is due to the addition of the zero offset voltage as described above.

DC signal 306 is delivered from amplifier 228 to a lock-in amplifier 230 for measurement. Lock-in amplifier 230 is also connected to AOM trigger 226 to activate lock-in amplifier 230 during the ring-down phase. Lock-in amplifier 230-requires a certain int egration period ftor determining the decay rate $1/\tau$. A person of average skill in the a rt will realize that this period will be limited by the gate width and that varying the gate width will present a trade-off between signal strength and signal-to-noise ratio. In the present embodiment a 50% duty cycle (i.e., when the gate width was equal to half the AOM switching period) yielded optimal signal intensity. Of course, optimal gate width setting with respect to the AOM switching period may have to be determined for each particular case.

The output of lock-in amplifier 230 yields the decay rate $1/\tau$. An optional digitizer 232 and a digital signal processing unit 234 can be connected to the output of lock-in amplifier 230. Unit 234 can be used to perform further calculations, statistical analysis of decay rate $1/\tau$ and absorption of sample 120 as discussed above. A display unit 236, such as a digital oscilloscope, is connected to unit 234, or, in the absence of digitizer 232 and unit 234 directly to lock-in amplifier 230 to display the results. For high precision measurement of the decay rate $1/\tau$ several ring-down phases may be measured at the same frequency of pump beam 122 before continuing the scan.

Lock-in amplifier 230 can also be replaced by a sample and hold circuit which.captures every ring-down and transmits these ring-downs to a digitizer. Thus, the averaging function of lock-in amplifier 230 is replaced by a fast digitizer and averaging on a computer. For very short decay constants (T<1 $\mu s$) this approach can be more favorable because the bandwidth of lock-in amplifier 230 is usually limited.

Figure 11:
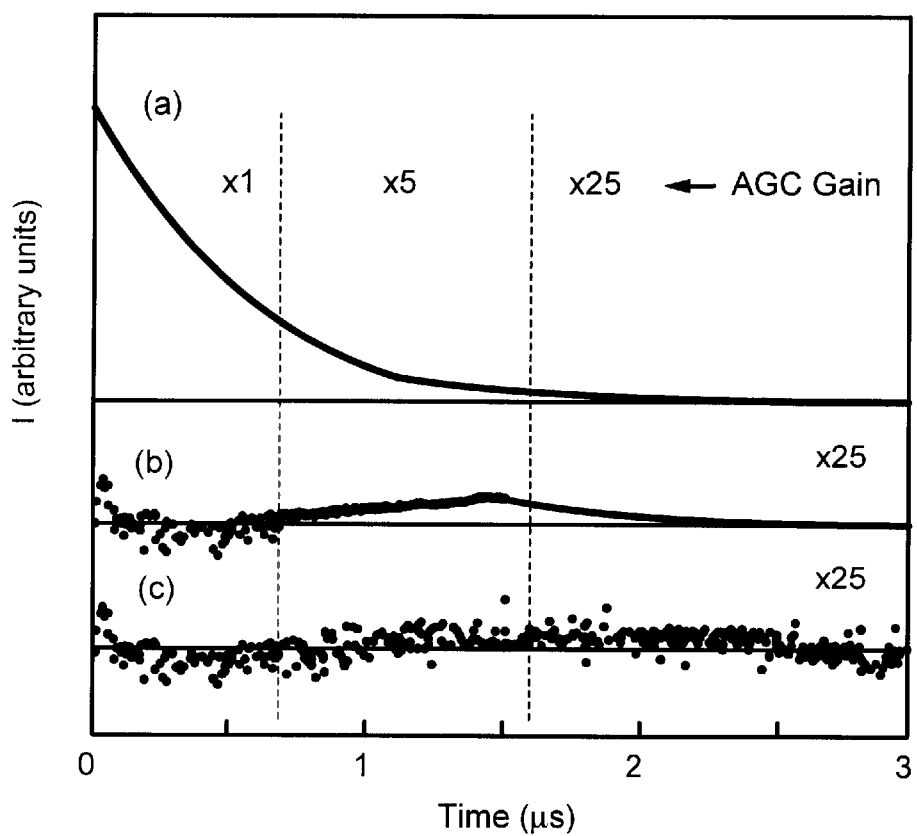
FIG. 11 is a graph illustrating the performance of a prior art detection circuit using a digitizer.

The performance of preferred CW CRDS arrangement 100 employing detection system 200 has been studied and compared to the performance of a prior art-digital detection system employing a 10-bit digitizer. FIG. 11 illustrates the performance of the prior art detection system used with optical measurement system 102 of CW CRDS arrangement 100. FIG. 11(a) shows a combined exponential decay composed of an initial unamplified decay and two regions obtained with additional amplification (×5, and ×25). These decays were recombined and fit to an exponential function in FIG. 11(a). In FIG. 11(b) the residual obtained by subtracting the experimental data from the fitted curve is shown on an expanded scale. For comparison, FIG. 11(c) shows a residual obtained for an unamplified waveform. The errors due to digitization are apparent from the signal scatter.

Figure 12A:
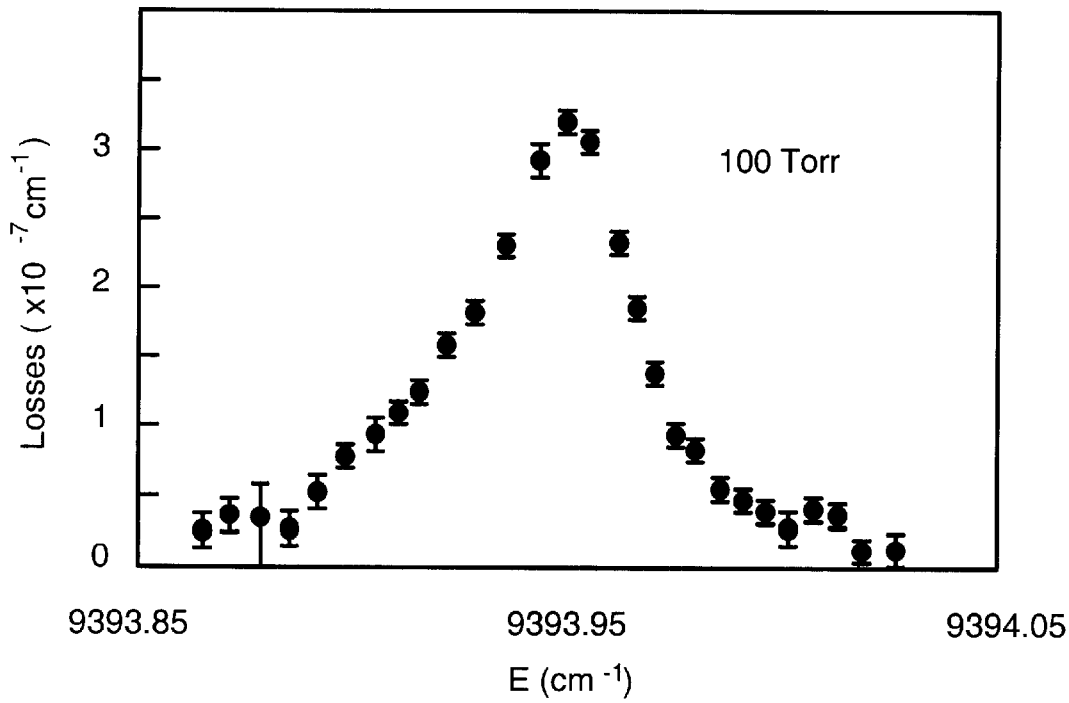
FIG. 12A is a graph illustrating the performance of a prior art detection circuit using a digitizer in studying a portion of the absorption spectrum of $CO_2$.

Furthermore, FIG. 12A shows the performance of this prior art detection system in scanning a sample 120 of $CO_2$ gas distributed throughout cavity 110 and maintained at a pressure of 100 Torr. The finesse of cavity 110 is 14,000, its empty ring-down time (baseline) is 3 $\mu s$ and the round-trip length between mirrors 112, 114 and 116 is 42 cm. The wavelength scanning range includes the absorption peak at 1064 nm and is indicated in terms of the wavenumber in this graph. The scan has an overall signal sensitivity of $7.7 \times 10^{-8}$ $cm^{-1}Hz^{-\frac{1}{2}}$ and requires approximately 40 minutes to complete. The sensitivity value is far above the theoretical shot-noise limit. Furthermore, this sensitivity value places a limit on the ability to detect trace gas concentrations. For example, $CO_2$ gas at less than 50 Torr could not be detected by the prior art CRDS arrangement employing a digitizer, whereas CW CRDS system 100 is capable of detecting $CO_2$ gas at 10 mTorr.

Figure 12B:
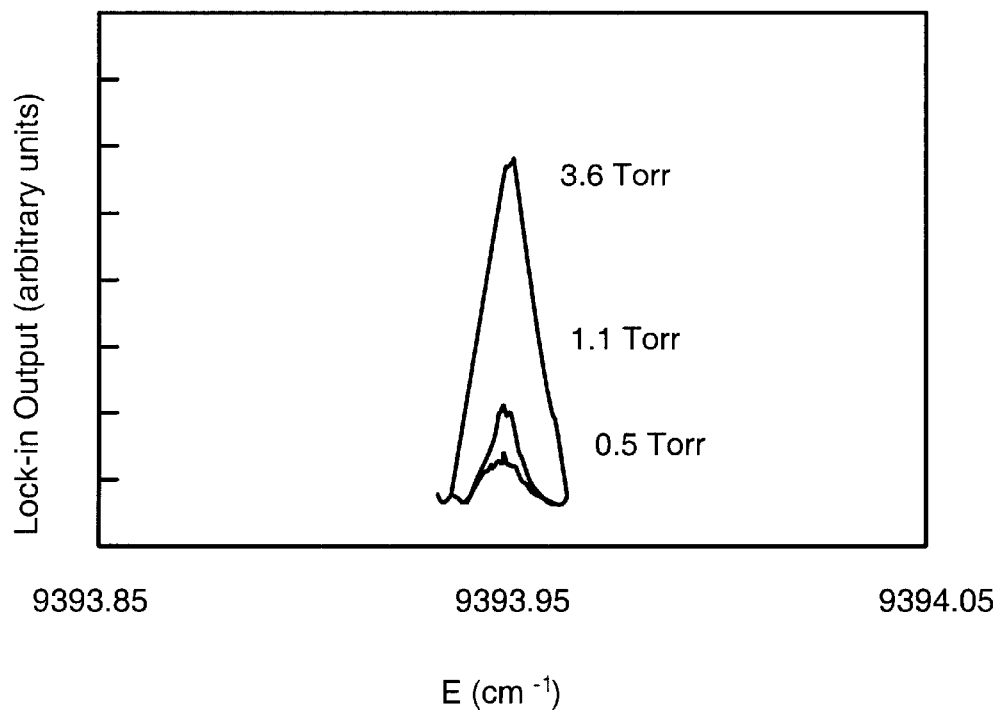
FIG. 12B is a graph illustrating the performance of the preferred embodiment in studying the same portion of the absorption spectrum of $CO_2$.

The performance of the preferred embodiment under the same conditions in obtaining the same scan of $CO_2$ gas over the same wavenumber range is shown in FIG. 12B. Because of the improved sensitivity it was possible to examine the $CO_2$ absorption peak at much lower pressures (concentrations); specifically at 3.6 Torr, 1.1 Torr and 0.5 Torr. The resolution of the scan is 75 kHz. The signal sensitivity is approximately $6 \times 10^{-11}$ $cm^{-1}Hz^{-\frac{1}{2}}$ and the scan requires approximately 8 seconds to acquire. The improvement in sensitivity over the prior art system is thus about three orders of magnitude and approaching the theoretical shot-noise limit for this arrangement.

Clearly, analog detection system 102 of the invention is superior to prior art digital systems not only because it approaches shot-noise level sensitivity, but also because it is fast. The repetition rates for measuring the decay rate $1/\tau$ are limited only by the time required for sufficient light buildup in cavity 110. In addition, system 102 is very reliable and can be implemented with other noise reducing measures used in CRDS.

The preferred embodiment can be altered in many ways without venturing beyond the scope of the invention. For example, ring-down beam may comprise the s-polarization and p-polarization of light or any polarizations supported by the ring-down cavity, as mentioned above. Also, various types of ring-down cavities, besides ring cavities can be implemented. Analog detection according to the invention can be implemented in systems where the laser line (laser frequency) is locked to the cavity line (cavity resonant frequency) or not. Furthermore, analog detection according to the invention can be employed in swept systems where the laser line is swept across the cavity line or where the cavity line is swept across the laser line, e.g., by adjusting the length of the cavity. A person of average skill in the art will recognize that any CRDS system can be adapted to the analog detection method of the invention.

Figure 13:
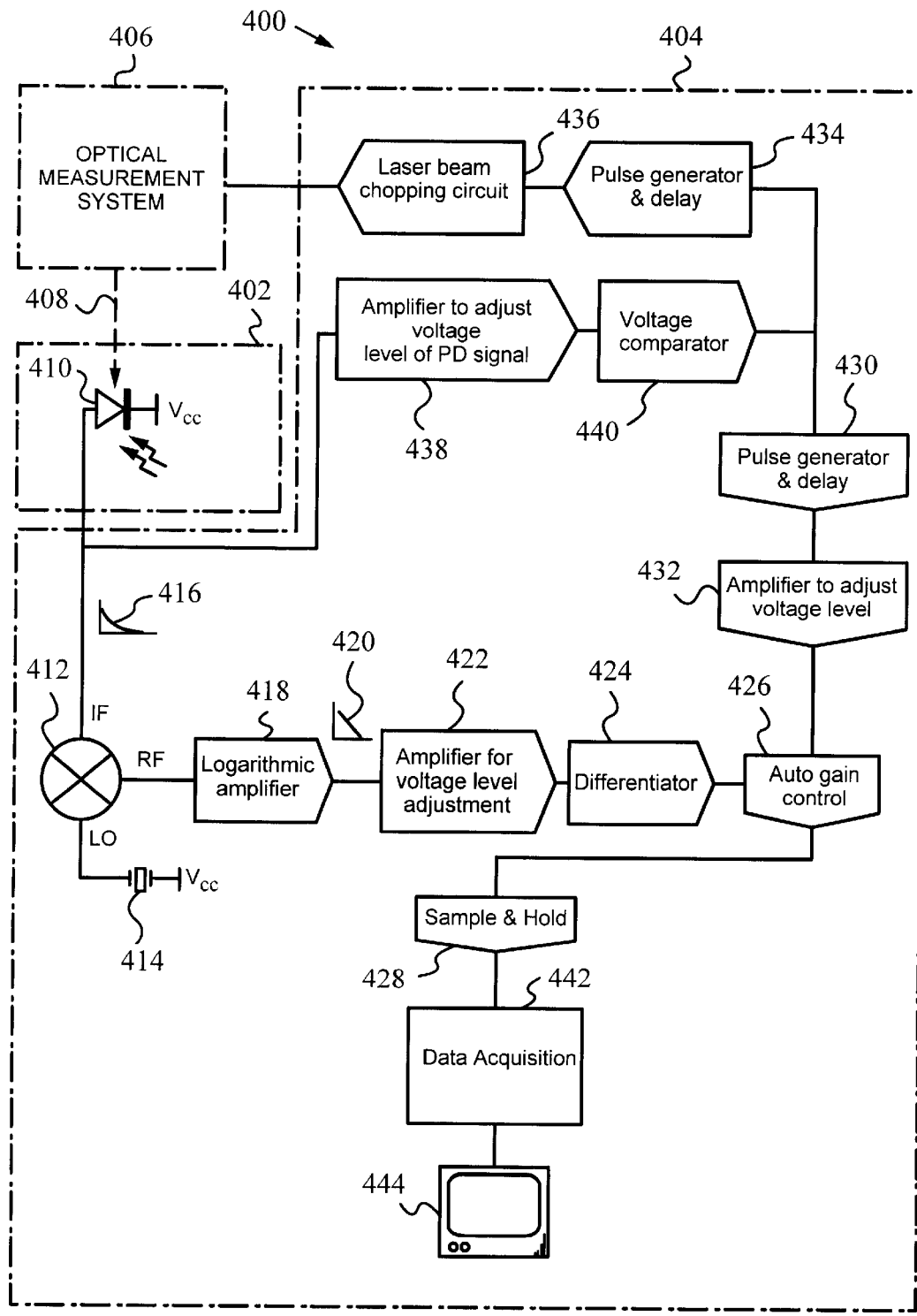
FIG. 13 is a block diagram of an alternative detection system according to the invention.

FIG. 13 shows a block diagram of an alternative analog detection system 400 made up of a photodetection sub-system 402 and a signal processing sub-system 404. An optical measurement system 406 providing a ring-down beam 408 can be similar to system 102 or different from it. In fact, system 400 is particularly well-suited for operation in swept-cavity CRDS.

Figure 14:
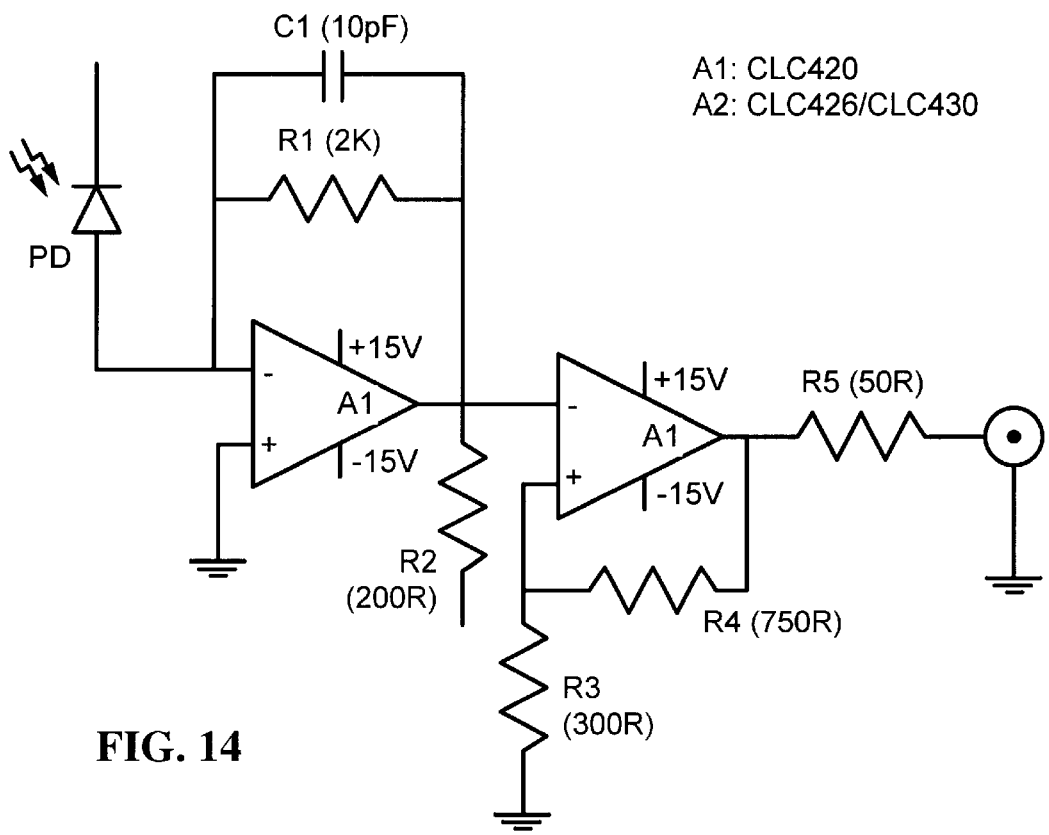
FIG. 14 is a circuit diagram of a photodetection subsystem.

Photodetection sub-system 402 has a photodetector 410 and associated amplification electronics as shown in FIG. 14.

Signal processing sub-system 404 has a mixer 412 supplied with an LO frequency by an oscillator 414. Mixer 412 is connected to photodetection sub-system. 402 for receiving an exponentially decaying analog signal 416 generated by photodetector 410 from ring-down beam 408 and amplified by the circuit of FIG. 14. The output of mixer 412 yields the up-converted analog signal 416 at an RF frequency.

A logarithmic amplifier 418 is connected to the output of mixer 412 for receiving the upconverted exponentially decaying analog signal 416 and transforming it to a linearly decaying analog signal 420. A voltage level adjustment amplifier 422 connected to logarithmic amplifier 418 compensates the voltage level of signal 420. A differentiator 424 differentiates signal 420 to produce a voltage corresponding to the slope of signal 420.

An AGC amplifier 426 is connected to differentiator 424 for receiving the slope value and passing it to a sample and hold circuit 428 when gated with the aid of a pulse generator and delay 430 and a voltage level amplifier 432. This occurs in the same manner as described in the preferred embodiment. Specifically, amplifier 432 controls the gain of AGC 426 as triggered by pulse generator and delay 430. The additional delay feature allows one to vary the onset of the gate and activate AGC 426 during a particular portion of exponentially decaying signal 416. This is advantageous when a particular portion of signal 416 is known to be more suitable for measurement of the decay rate $1/\tau$, e.g., because of lower noise content.

A separate pulse generator and delay 434 supply a triggering signal to a laser beam chopping circuit 436. Chopping circuit 436 drives a chopper (not shown) which controls the ring-down of a ring-down cavity contained in optical measurement system 406. In this embodiment optical measurement system 406 is a swept-cavity type system. Accordingly, the laser's wavelength is tuned until build-up of light inside the cavity occurs. The build-up appears as an increasing signal on photodetector 410 while the ring-down phase produces ring-down signal 416.

An amplifier 438 amplifies signal 416 and compares it to a preset level with the aid of a voltage comparator 440 connected to amplifier 438. When the level of signal 416 exceeds the preset level the ring-down phase is initiated by chopping circuit 436 for a time determined by pulse generator and delay circuit 434. In other words, circuit 434 is set to determine the length of the ring-down phase. Chopping circuit 436 initiates the ring-down phase by either turning off the laser current, i.e., turning the laser off directly, deflecting the laser beam with the aid of an acousto-optic modulator, or modulating the wavelength of the laser beam.

Sample and hold circuit 428 delivers the value of the decay rate $1/\tau$ averaged over the gate width to a data acquisition unit 442. Unit 442 performs statistical computations and absorption calculations on the value received from 428 with or without digitizing the signal. Specifically, unit 442 computes the absorption loss of the ring-down cavity. When no sample is present in the cavity this absorption loss corresponds to the cavity baseline. When an absorptive sample is present, the baseline absorption is subtracted from the signal to obtain the absorption of the sample. The results are displayed on a display unit 444.

The advantages of this embodiment over the preferred embodiment are that there are fewer components and that it can work with any general ring-down system. For example, analog detection system 400 can be used in CW CRDS operating with ring-down cavities which are not locked to the laser.

Furthermore, system 400 can be used in a P CRDS arrangement. Every time a laser pulse is produced in a P CRDS arrangement the laser will produce a trigger signal. This trigger signal is equivalent to the one produced by elements 438 and 440 of FIG. 13. Hence, in the P CRDS arrangement elements 438 and 440 are omitted. Additionally, elements 436 and 434 are also not required, since the laser pulse turns itself off automatically. In a further simplification of system 400 for P CRDS, trigger signal can directly trigger sample and hold circuit 428 through pulse generator 430. Hence, AGC 426 can be omitted as well.

In an alternative method of determining the decay constant $\tau$, the measurement can be performed on the signal obtained from the ring-down cavity during the light build-up phase or the ring-up phase. That is because the ring-up rate depends on decay constant τ of the ring-down cavity. The ring-up measurement can be performed with any of the analog detection systems described above. However, rather than measuring the ring-down beam these systems are gated or turned on to perform their measurements while receiving the ring-up beam during the ring-up phase. The growth or increase in intensity of the ring-up beam generates an exponentially growing analog signal. Upon conversion of this exponentially growing analog signal to a linear analog signal, its slope and therefrom its build-up rate are calculated.

Figure 15:
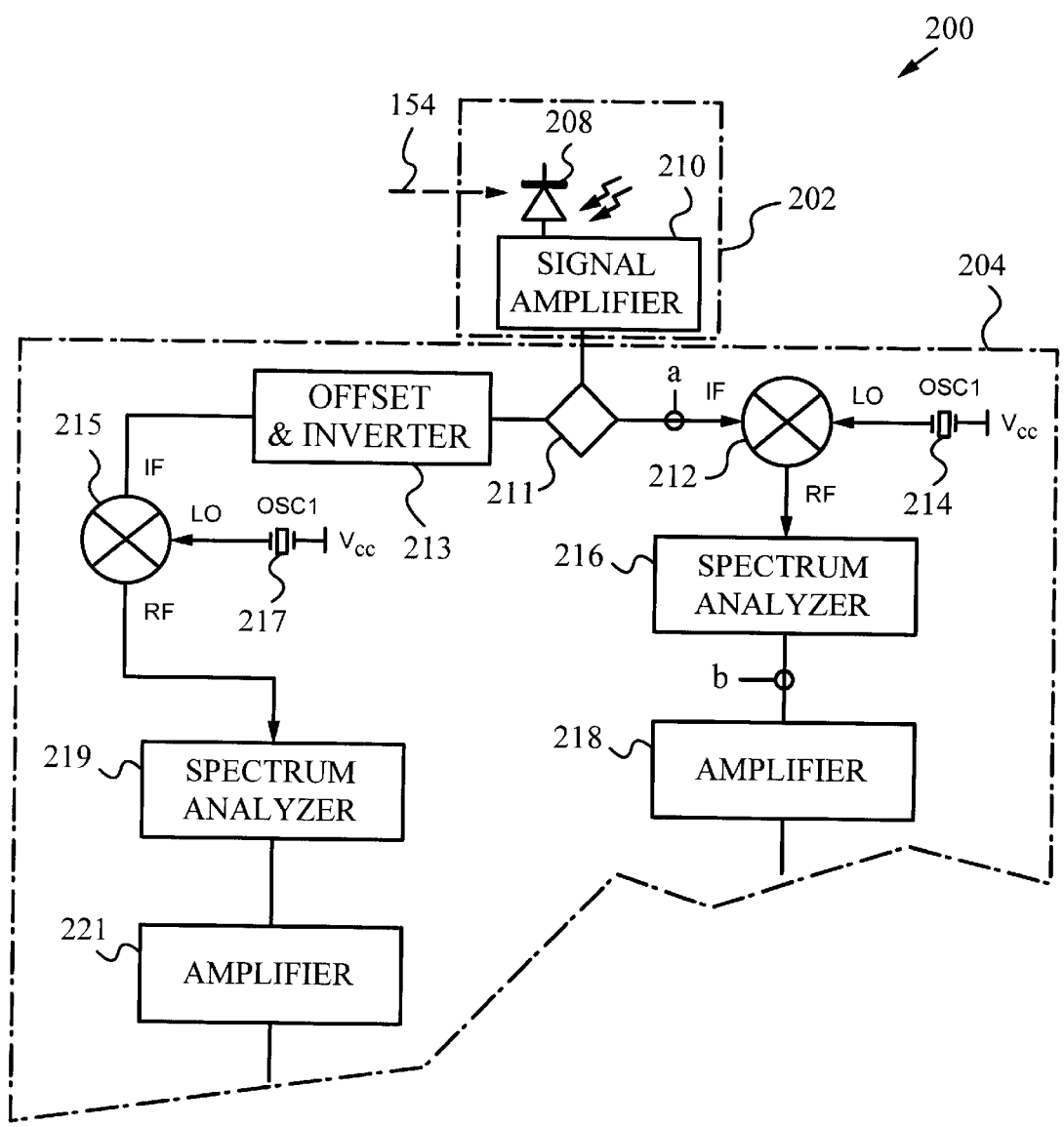
FIG. 15 is a block diagram of a portion of the detection system of FIG. 4 adapted for determination of ring-up and ring-down rates.

System 200 of FIG. 4 can be easily adapted for determination of the ring-up rate. In fact, FIG. 15 shows a portion of analog detection system 200 adapted to make measurements of both the ring-up rate and the ring-down rate. The same reference numerals are used to refer to the same elements. The corresponding signals are shown in the graph of FIG. 5.

It should be noted that system 200 operates with ring-down cavity 110 with is locked to laser 118. Because of intensity fluctuations during ring-up, laser to cavity locking or any other means of ensuring smooth light build-up in the ring-down cavity is required when using ring-up analog detection.

The output of low noise amplifier 210 is connected to a gate 211 which is triggered to pass electrical signal 300 to mixer 212 during the ring-down phase. In other words, gate 211 passes only exponentially decaying analog signal 300A to mixer 212, as described above. During the ring-up phase, i.e., during portion 300B of signal 300 gate 211 passes signal 300B to offset and inverter circuit 213. For convenience, gate 211 may use the trigger signal from function generator 224 to control gate 211.

The exponentially growing form of signal 300B is described by the expression $1-e^{-t/\tau}$. Thus, the ring-up rate is governed by the same decay constant τ as the ring-down rate. Offset and inverter 213 offsets signal 300B by subtracting 1 from it and then inverts it through multiplication by −1. In fact, the circuit shown in FIG. 9 can be employed to perform the operation of offset and inverter 213.

The resulting offset and inverted signal 300B' is indicated by a dashed line in FIG. 5 and is equivalent in form to ring-down signal 300A. Hence, the ring-up rate can be determined by performing the same operations on signal 300B' as performed on signal 300A.

Specifically, signal 300B' is mixed in a mixer 215 with an LO frequency provided by an oscillator 217 and passed on to a spectrum analyzer 219. Spectrum analyzer 219 converts the exponentially decaying form of signal 300B' to a linearly decaying analog signal and sends it to amplifier 221. All the remaining operations leading to determination of ring-up rate 1/τ are the same as for signal 300A, as described above. Thus absorption of sample 120 can be derived from the ring-up rate as well as from the ring-down rate. The absorption values obtained during ring-up detection and ring-down detection can be compared and averaged if desired.

Although in this embodiment separate mixers 212, 215 and oscillators 214, 215 are used, it is possible to design a circuit which uses mixer 212 and oscillator 214 for both signals 300A and 300B. A person of average skill in the art will be able to design the appropriate circuitry.

It will be clear to one skilled in the art that the above embodiments may be altered in many ways without departing from the scope of the invention. Accordingly, the scope of the invention should be determined by the following claims and their legal equivalents.

What is claimed is:

1. An analog detection system for determining a decay rate of an exponentially decaying ring-down beam issuing from a ring-down cavity during a ring-down phase, said detection system comprising:

a) a photodetector for receiving said ring-down beam and generating an exponentially decaying analog signal;

b) a converter for converting said exponentially decaying analog signal to a linear analog signal having a slope indicative of said decay rate; and c) an analog signal processing circuit for determining said slope and said decay rate.

2. The analog detection system of claim 1, further comprising a control element for activating said analog detection system during said ring-down phase.

3. The analog detection system of claim 1, wherein said ring-down cavity is pumped by a pump beam from a pump laser.

4. The analog detection system of claim 3, wherein said pump laser is a pulsed laser.

5. The analog detection system of claim 3, further comprising a frequency adjustment element for altering the frequency of said pump beam.

6. The analog detection system of claim 3, wherein said pump laser is a continuous wave laser.

7. The analog detection system of claim 6, further comprising a chopping means for interrupting said pump beam during said ring-down phase.

8. The analog detection system of claim 3, wherein said pump beam comprises a predetermined polarization.

9. The analog detection system of claim 1, wherein said ring-down cavity comprises an absorptive sample for altering said decay rate.

10. The analog detection system of claim 1, further comprising a triggering means for activating said analog detection system during a predetermined portion of said exponentially decaying analog signal.

11. The analog detection system of claim 1, wherein said analog signal processing circuit converts said decay rate to a decay rate voltage and said analog detection system further comprises a means for converting said decay rate voltage to an absorption loss of said ring-down cavity.

12. An analog detection system for determining a ring-up rate of an exponentially building ring-up beam issuing from a ring-down cavity during a ring-up phase, said detection system comprising:

a) a photodetector for receiving said ring-up beam and generating an exponentially growing analog signal;

b) a converter for converting said exponentially growing analog signal to a linear analog signal having a slope indicative of said ring-up rate; and c) an analog signal processing circuit for determining said slope and said ring-up rate.

13. The analog detection system of claim 12, further comprising a control element for activating said analog detection system during said ring-up phase.

14. The analog detection system of claim 12, wherein said ring-down cavity is-pumped by a pump beam from a pump laser.

15. The analog detection system of claim 14, further comprising a locking means for locking said pump laser to said ring-down cavity.

16. The analog detection system of claim 14, wherein said pump beam comprises a predetermined polarization.

17. The analog detection system of claim 14, wherein said pump laser is selected from the group consisting of continuous wave lasers and pulsed lasers.

18. The analog detection system of claim 12, wherein said ring-down cavity comprises an absorptive sample for altering said ring-up rate.

19. The analog detection system of claim 12, further comprising a triggering means for activating said analog detection system during a predetermined portion of said exponentially growing analog signal.

20. The analog detection system of claim 12, wherein said analog signal processing circuit converts said ring-up rate to a ring-up rate voltage and said analog detection system further comprises a means for converting said ring-up rate voltage to an absorption loss of said ring-down cavity.

* * * * *

UNITED STATES PATENT AND TRADEMARK OFFICE
CERTIFICATE OF CORRECTION

PATENT NO. : 6,532,071 B2  Page 1 of 1
DATED : March 11, 2003
INVENTOR(S) : Richard N. Zare et al.

It is certified that error appears in the above-identified patent and that said Letters Patent is hereby corrected as shown below:

Column 1,
Line 14, change "DE-FG03-92ER14303" to -- DE-FG03-92ER14304 --.

Signed and Sealed this

Eleventh Day of April, 2006

JON W. DUDAS
*Director of the United States Patent and Trademark Office*